US012683009B2

(12) United States Patent
Gupta et al.

(10) Patent No.: US 12,683,009 B2
(45) Date of Patent: Jul. 14, 2026

(54) COGNITIVE LOAD ASSISTANCE METHOD AND SYSTEM

(71) Applicant: Sony Interactive Entertainment Inc., Tokyo (JP)

(72) Inventors: Rajeev Gupta, London (GB); Jason Craig Millson, London (GB); Mark Jacobus Breugelmans, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 241 days.

(21) Appl. No.: 18/452,166

(22) Filed: Aug. 18, 2023

(65) Prior Publication Data
US 2024/0071603 A1 Feb. 29, 2024

(30) Foreign Application Priority Data
Aug. 25, 2022 (GB) ..................................... 2212376

(51) Int. Cl.
*G16H 20/70* (2018.01)
*G06F 9/451* (2018.01)

(52) U.S. Cl.
CPC ............. *G16H 20/70* (2018.01); *G06F 9/453* (2018.02)

(58) Field of Classification Search
CPC ......... G16H 20/70; G06F 9/453; G06F 3/011; G06F 9/451; A63F 13/69; A63F 13/79; A63F 13/53
See application file for complete search history.

(56) References Cited

U.S. PATENT DOCUMENTS

| | | | |
|---|---|---|---|
| 6,714,963 B1 | 3/2004 | Levine | |
| 2003/0046401 A1* | 3/2003 | Abbott | G06F 9/451 |
| | | | 709/227 |
| 2011/0055267 A1* | 3/2011 | Bolger | A63F 13/30 |
| | | | 715/757 |
| 2013/0152001 A1 | 6/2013 | Lovit | |
| 2014/0350941 A1* | 11/2014 | Zeigler | G10L 15/19 |
| | | | 704/275 |
| 2018/0286272 A1 | 10/2018 | McDermott et al. | |
| 2021/0055841 A1* | 2/2021 | Pruitt | G06F 3/013 |
| 2024/0085975 A1* | 3/2024 | Alailima | G06F 3/011 |

FOREIGN PATENT DOCUMENTS

| | | |
|---|---|---|
| WO | 2015127361 A1 | 8/2015 |
| WO | 2015167847 A1 | 11/2015 |

OTHER PUBLICATIONS

Combined Search and Examination Report for corresponding GB Application No. 2212376.4, 5 pages, dated Feb. 10, 2023.
Extended European Search Report for corresponding EP Application No. 23190547.2, 11 pages, dated Jan. 3, 2024.
Office Action in European Appln. No. 23190547.2, mailed on Jun. 10, 2025, 9 pages.

* cited by examiner

*Primary Examiner* — King Y Poon
*Assistant Examiner* — Patrick P Galera
(74) *Attorney, Agent, or Firm* — Fish & Richardson P.C.

(57) ABSTRACT
A cognitive load assistance method includes: providing a virtual environment comprising a route to complete a current task, and providing within the virtual environment one or more interactive elements not essential to the current task that may be encountered during normal performance of the current task, receiving an indication that cognitive load assistance is required, and reducing the interactivity of at least a first interactive element not essential to the current task in response to the indication.

16 Claims, 3 Drawing Sheets

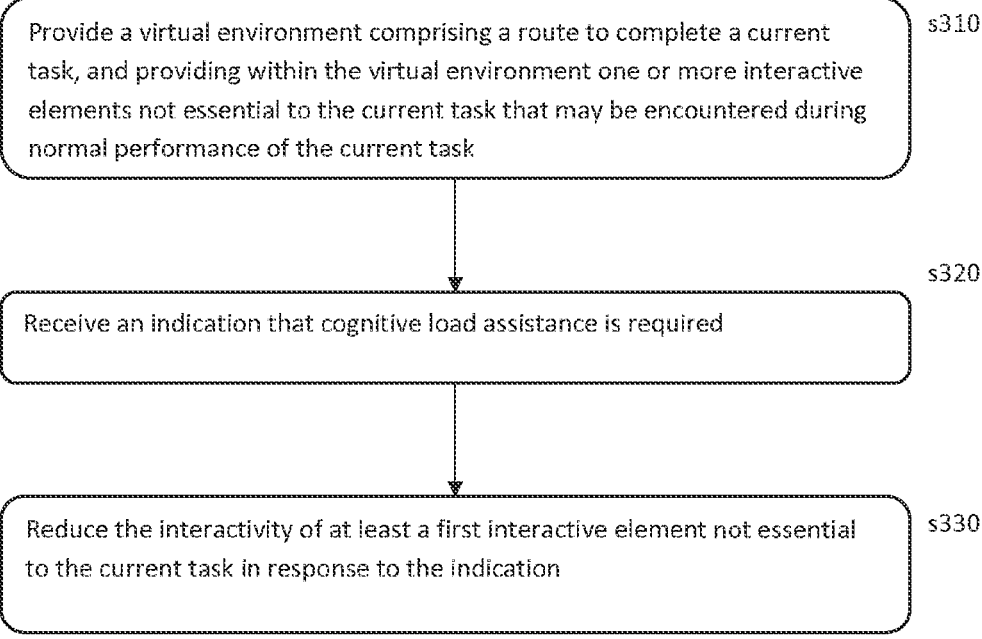

Provide a virtual environment comprising a route to complete a current task, and providing within the virtual environment one or more interactive elements not essential to the current task that may be encountered during normal performance of the current task          s310

Receive an indication that cognitive load assistance is required          s320

Reduce the interactivity of at least a first interactive element not essential to the current task in response to the indication          s330

Figure 3

COGNITIVE LOAD ASSISTANCE METHOD AND SYSTEM

BACKGROUND OF THE INVENTION

Field of the Invention

The present invention relates to a cognitive load assistance method and system.

Description of the Prior Art

There are a wide variety of video game genres, with some providing very focused and linear play (e.g. racing games, so-called arcade type games, and the like) whilst others provide complex and open ended play (e.g. so-called role playing games, open-world games, and the like). Similarly there are non-gaming computer activities that are very focused and linear (e.g. in data entry, or scripted activities) and others that are potentially complex and open ended (e.g. use of a word processor, or navigating a file manager).

For people who have difficulties with cognitive loads (for example in terms of handling complex task sequences or maintaining focus on a task within a complex environment), the latter type of game or computing activity can be difficult and unenjoyable.

Embodiments of the present invention aim to mitigate or alleviate this problem.

SUMMARY OF THE INVENTION

Various aspects and features of the present invention are defined in the appended claims and within the text of the accompanying description.

In a first aspect, a cognitive load assistance method is provided in accordance with claim 1.

In another aspect, a cognitive load assistance system is provided in accordance with claim 15.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3 is a flow diagram of a cognitive load assistance method in accordance with embodiments of the present description.

DESCRIPTION OF THE EMBODIMENTS

A cognitive load assistance method and system are disclosed. In the following description, a number of specific details are presented in order to provide a thorough understanding of the embodiments of the present invention. It will be apparent, however, to a person skilled in the art that these specific details need not be employed to practice the present invention. Conversely, specific details known to the person skilled in the art are omitted for the purposes of clarity where appropriate.

Figure 1:
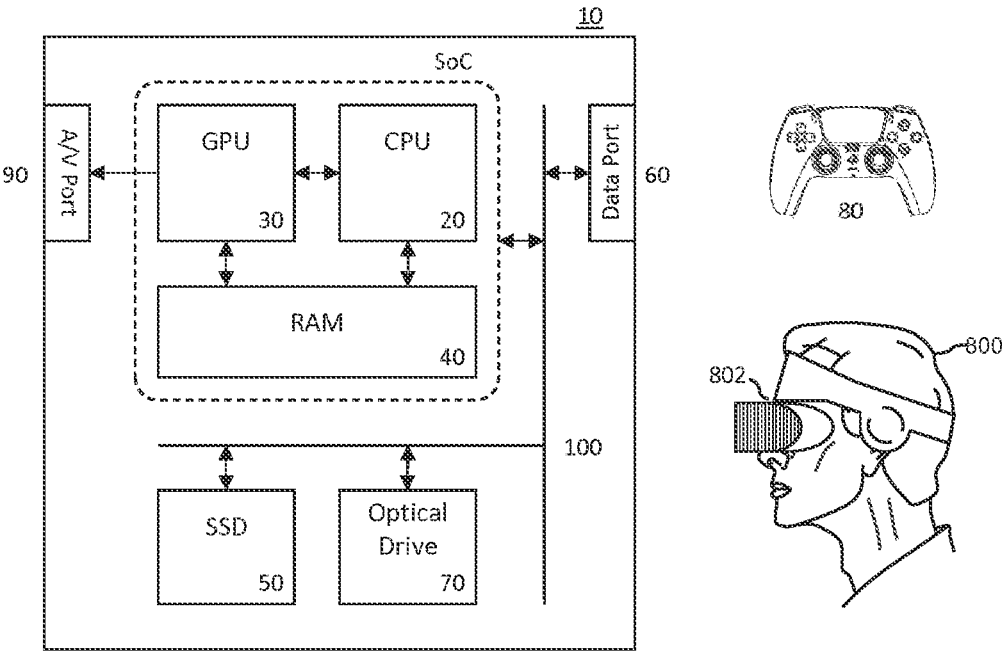
FIG. 1 is a schematic diagram of a cognitive load assistance system in accordance with embodiments of the present description.

Referring now to the drawings, wherein like reference numerals designate identical or corresponding parts throughout the several views, FIG. 1 shows an example of an entertainment system 10 as a computer or console such as the Sony® PlayStation 5® (PS5).

The entertainment system 10 comprises a central processor 20. This may be a single or multi core processor, for example comprising eight cores as in the PS5. The entertainment system also comprises a graphical processing unit or GPU 30. The GPU can be physically separate to the CPU, or integrated with the CPU as a system on a chip (SoC) as in the PS5.

The entertainment device also comprises RAM 40, and may either have separate RAM for each of the CPU and GPU, or shared RAM as in the PS5. The or each RAM can be physically separate, or integrated as part of an SoC as in the PS5. Further storage is provided by a disk 50, either as an external or internal hard drive, or as an external solid state drive, or an internal solid state drive as in the PS5.

The entertainment device may transmit or receive data via one or more data ports 60, such as a USB port, Ethernet® port, Wi-Fi® port, Bluetooth® port or similar, as appropriate. It may also optionally receive data via an optical drive 70.

Interaction with the system is typically provided using one or more handheld controllers 80, such as the DualSense® controller in the case of the PS5.

Audio/visual outputs from the entertainment device are typically provided through one or more A/V ports 90, or through one or more of the wired or wireless data ports 60.

Where components are not integrated, they may be connected as appropriate either by a dedicated data link or via a bus 100.

An example of a device for displaying images output by the entertainment system is a head mounted display 'HMD' 802, worn by a user 800.

The cognitive load assistance system or the method implementing that system may be implemented either at a system (i.e. operating system or helper app) level or at an in-game level, or a combination of the two, for example on the entertainment system 10 of FIG. 1.

For example, a user may have an accessibility profile associated with their account, which includes information relevant to whether to use a cognitive load assistance system. For example, a user profile may note that a user has attention deficit hyperactivity disorder (ADHD), which means that they may find it relatively more difficult to maintain focus on a current in-game quest, task, aim, or goal (more generally, a 'current task').

Similarly a user profile may note that a user has difficulties with memory retention, or lapses in concentration, associated with the early symptoms of dementia or Alzheimer's disease, that again may mean they find it relatively more difficult to maintain focus on a current task.

Similarly a user profile may indicate that the user is very young, which again may mean they find it relatively more difficult to maintain focus on a current task.

Other examples will be apparent to the skilled person.

The information in the accessibility profile (or equivalently, an indication of what assistance or mitigation system is required, such as the presently described cognitive load assistance system) may be provided to the game via a system API.

If an accessibility profile is not available, optionally either the system or the game may prompt the user to input details about themselves to provide corresponding information.

This information may be made persistent (e.g. added to the user profile) or temporary (e.g. if the user is a guest user on a system).

Optionally quick profiles may be provided within an accessibility option accessible either in the system or the game—for example under headings such as cognitive, motor, and sensory, and then common conditions and issues such as memory/attention in cognitive, arthritis in motor, and colour blindness in sensory. A user can select the relevant options to quickly build a profile.

Embodiments of the present description seek to assist users with memory/attention difficulties (for example as indicated by their accessibility profile) when playing a game that has a current task that has been selected either by the user or by the game itself.

Figure 2:
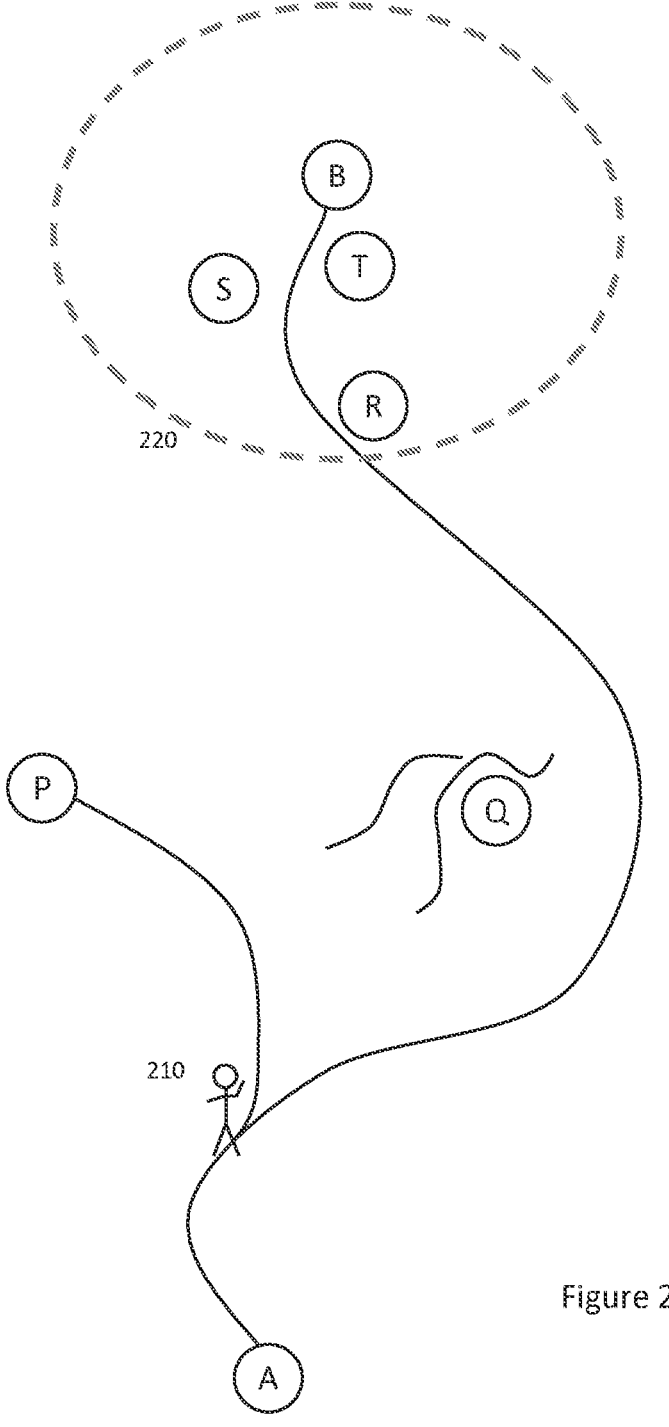
FIG. 2 is a schematic diagram of a task path comprising a plurality of distractions, in accordance with embodiments of the present description.

Referring now to FIG. 2, a current task may involve, as a non-limiting example, the user traversing a virtual environment from current position A to goal position B, along the path illustrated by the line between these points.

Conventionally, along the route the user may encounter an active task distraction in the form of a non-player character 210, who asks them for help, resulting in an optional side quest P. The user may also encounter a passive task distraction in the form of a cave Q or other environmental feature some way off the path that may be tempting to explore.

Finally, the goal position B is inside a city that (in order to create the impression of a busy world) has a high density of quests or interactive characters, such as city guard R, shopkeeper S, or thief T, that may be encountered before reaching the goal location B.

Any or all of these distractions could prevent the user from reaching goal B directly, or at least within a current gaming session, and cause the user to forget to complete task B or have difficulty returning to it, or recalling its requirements or the like.

Accordingly, in embodiments of the present description a cognitive load assistance system selectively removes or downgrades in-game distractions from the current task. The number of distractions to remove or downgrade may be a function of a variety of factors described later herein, but may include the number of distractions in the path to the goal, the types of distractions, the degree of assistance the user may require (for example as indicated by their accessibility profile/the API), a user preference such as a slider for reducing distraction, and the time available in a current gaming session to possibly complete the task (for example in the case of a child with a parentally set gaming time).

A typical order of priority for removing or downgrading distractions that mitigates the greatest distractions first could be: (i) remove or downgrade active task interruptions, (ii) remove or downgrade interactive characters, (iii) reduce the density of distractions, and (iv) remove or downgrade passive task interruptions.

Whilst removal is self-explanatory, downgrading may depend on the type of distraction. For example an active task distraction could be downgraded to a passive distraction by moving the character 210 from on the path to beside of the path, and only revealing side quest P if the user choses to interact with the character first. Alternatively, the character 210 could actively intercept the player, but then ask them to come back once they have completed their current quest; and a quest stub to return to the character could be added as an addendum to the current quest, or as a pending quest.

Similarly for other interactive characters, guard R may not challenge the user upon entry to the city, shopkeeper S may not announce they are a shop keeper, and thief T may not attempt to steal anything, until after the goal B has been reached. In other words, their interactivity is curtailed.

It will be appreciated that interactive characters may be classed as active or passive distractions based on whether they actively approach or force an interaction upon the user versus whether they merely announce their existence. Hence for example a shopkeeper may be passive if they just call out to the user, whilst a guard may be active if they block the user's entry.

In addition distractions, particularly those of interactive characters, may be classified as short or long; the city guard is short; you either talk to the guard or fight them to enter, and then you have passed that point. Meanwhile the shopkeeper may be long if they provide materials that cause the user to spend time in their inventory, or changing their focus (for example if a new sword or portion is available that would allow the user to do something else), or short if they provide generic goods (e.g. a pub landlord that only sells food and drink used for health); similarly the thief may be long if they encourage the user to chase them and return the stolen goods. More generally, interactive characters that either trigger active task distractions or create/cause/lead to tasks of their own may be considered 'long', whilst interactive characters that have a small degree of interaction or only interact in one or a small number of ways within the immediate environment of the game can be considered 'short'.

Hence interactive characters can be potentially active and long, active and short, passive and long, or passive and short. More generally passive environmental elements such as cave Q can be similarly thought of as passive and long (if a large cave and/or containing further activities just as puzzles or more quests) or passive and short (if a small cave and/or containing no activities, e.g. just collectibles).

Such a classification may be used along the path to choose what distractions to remove or downgrade, but particularly in areas with a high density of distractions such as in the city; here the overall density of distractions may be reduced whilst still keeping some present, to maintain the appearance of an interactive world. in this case long distractions may be dropped or downgraded (for example curtailing interactions or activities associated with the 'long' components of their behaviour), whilst short distractions are maintained to provide a sense of life but with less scope to take the user off the intended path.

Meanwhile passive task distractions such as environmental elements like the cave can similarly be removed, but this can be problematic particularly for users with concentration or memory problems, as it may cause anxiety or confusion if cave Q is not visible during the current task but is then present when the user is later between tasks (or on a task that involves cave Q). Hence more preferably passive task interruptions are downgraded by making them inaccessible. Typically this may be achieved by locking a door or adding detritus to block access to a cave, or removing a dialog option from an interactive character that might lead to another task.

Whilst in principle any order or mix of removal or downgrade of distraction may be employed, as noted previously herein preferably firstly some or all active distractions proximate to the path between A and B may be removed or downgraded to passive. In this case proximate may mean visible or audible to the user when on the path, and/or arranged so as to be triggered when the user passes them on the path.

This alone may be considered a sufficient assistance to cognitive load for the user (an evaluation of which is discussed later herein). Optionally however secondly and as noted previously herein some or all interactive characters proximate to the path between A and B may be removed or downgraded, for example with 'some' corresponding to characters classed has active and/or having long distractions, and 'all' further including those that are passive and/or with short distractions.

Again this further modification may be considered a sufficient assistance to cognitive load for the user. However optionally thirdly and as noted previously herein some or all passive task interruptions proximate to the path between A and B may be downgraded, or less preferably removed. Downgrading typically comprises keeping the passive task interruption visible, but preventing access and/or interaction whilst the task of reaching location B is still active.

As noted previously, the extent to which such distractions are removed or downgraded can be assessed based on one or more of a number of criteria.

Optionally, task distractions may be awarded a score based on the level of distraction they represent. As a non-limiting example the following scores could be used:

| Distraction type | Score | Removal score | Downgrade Score |
|---|---|---|---|
| Active long (P, T) | 10 | 0 | 5 |
| Active short (R, S) | 5 | 0 | 2 |
| Passive long | 5 | 0 | 0 |
| Passive short (Q) | 2 | 0 | 0 |

In the above scheme, downgrading means making active distractions passive, and making passive distractions inaccessible (e.g. by use of physical blocks or limiting dialogue options). The distractions in FIG. 2 are listed for their respective types in the example scenario. It will be appreciated that a distraction score may be assigned based on such a type classification, or may be assigned to individual task distractions, for example based on play-throughs by game testers (e.g. as function of how often users are distracted by a distraction, and for how long).

In a first instance, the system may set a maximum amount of distraction on the path, for example as a maximum distraction score of 20. The current distractions add up to a score of 32, and so some distractions should be removed or downgraded.

There are several strategies for doing this. In one strategy the fewest distractions are changed by removing the highest scoring distractions—in this case, removing quest P and thief T. However, this completely removes access to their content, at least during the current quest—and for some content (for example quest P) if the user does not revisit the area containing the interactive character 210, they may lose all opportunity to play this quest.

In another strategy, content is preserved where possible by downgrading. In this case, downgrading P, T, and R or S bring the total under the target maximum of 20. Clearly optionally choosing downgrades that have the largest differential score first may be preferable in this case.

In a refinement of either strategy, distractions earlier along the path are removed or downgraded before later distractions, as users may be more easily distracted when the goal is more distant. Hence in this case, removing P and downgrading Q meets the target maximum of 20.

It will be appreciated that these strategies can be combined. Hence for example to preserve content, rather than removing quest P, the long active distractions can be downgraded first and then the remaining cases can be downgraded in path order, so that P and B are downgraded and then Q (rather than S or T) to meet the target maximum.

Again, if downgrading all distractions is not enough to reach the target maximum, then removing distractions either in path order or in order of largest score differential may be employed to reach the target maximum.

Using the above strategies, a maximum degree of distraction on the current quest can be achieved. This maximum can then be adjusted to suit the user and their circumstances. For example the API may provide a value in response to the accessibility profile of the user, with users reporting greater difficulties (or younger ages) having lower maximum scores. Alternatively the value may be computed by the game in response to the API or to the accessibility profile or an in-game accessibility assessment or report, as appropriate.

Similarly, the maximum target may change dynamically; if the user is still being distracted by downgraded or passive distractions, then the system may downgrade further distractions or remove already downgraded distractions further along the path.

More generally, the maximum target may change dynamically in response to the time taken to progress the current quest in the current play session. Optionally an estimate of the time to complete the quest may be obtained (for example from telemetry gathered during play testing), and if the user is taking more than a threshold period of time longer than the estimate, the maximum target may be reduced and the in-game distractions downgraded or removed accordingly. Similarly optionally where a fixed play session is set (either by the user themselves or by a supervising parent or guardian), then if progress along the path does not roughly equate with progress through the time allowed, or progress falls more than a threshold percentage behind progress through the time allowed, or the remaining time falls below the threshold amount, or any combination of these, then the maximum target may be reduced and the in-game distractions downgraded or removed accordingly.

Hence the maximum target value may be adjusted in response to the accessibility profile of the user and/or in response to their observed behaviour and/or rate of progress, either against expectation or against a set clock.

Other causes of dynamic adjustment include if the environment has randomised elements; if a creature is spawned randomly, this may represent an active or passive distraction, and the adjustments for the task may be re-evaluated. Alternatively, such randomised elements may be re-run until the result falls within the target maximum distraction value, or such an element may be suppressed (i.e. removed before it is included). This approach may also be used for environments that are built procedurally, dynamically adjusting the planned environment according to its effect on the target maximum distraction value until an suitable environment is achieved.

It will be appreciated that different tasks have different lengths and may pass through different types of environments with different numbers of distractions. Hence the above target maximum may optionally be interpreted as a target maximum per unit of path travelled, where a unit is a block of 10 minutes, or 30 minutes, or an in-game kilometre of terrain; in this way, the scheme can scale to different quests. Optionally, some areas within the game may have target multipliers to allow for a higher maximum that what is otherwise set, because more distractions are a desired feature; for example the city may have such a multiplier.

Alternatively, the target maximum can be relative rather than absolute; for example reducing distractions on the quest path (or unit part thereof) by 25% or 50% of their current total score.

The two approaches (relative and absolute) can be combined so that for example there is an N % reduction of distraction score until this level falls below an absolute value, so that there is always some semblance of in-game activity for the user, without being too distracting.

Once the user has completed the task, the above system may be reset so that the downgraded or removed tasks are restored. Optionally this may be done in a phased manner (e.g. over several minutes, or as a function of proximity to the user), so that for example the user is not overwhelmed by half a dozen shopkeepers suddenly all vying for the user's attention simultaneously.

Often one task (or subtask) segues immediately into another task or subtask. In this case again the system is reset, and distractions for the new task path are calculated.

Where a task can be achieved in several ways, or along several paths, the system can be modified further.

For example, suppose that the path leading to quest P also continued on to the guard at the city gate and was a valid alternative path for completing the current quest. Then depending on which route the user choses, different sets of distractions would be modified. Where a user has yet to choose one of a plurality of paths, the maximum total and the modification of distractions can be based on the most common path taken, or based on a probability-weighted assessment of all the distractions on all the available paths. The probabilities can again be ascertained from play-throughs by game testers.

Whilst the system and techniques herein have been described with reference to a videogame, it will be appreciated that the approach may be applied to any multi-step computing task. Typically for a complex task, the solution is to provide a so-called wizard that is exclusively focused on that one task. However, this can be limiting and potentially problematic if a user needs to exit that task to do something else (for example in response to a phone call).

Accordingly in embodiments of the present invention a similar approach is used for an application environment as to a game environment, with task distractions being menu tabs, icons, menu items, pop-ups, contextual menu elements etc., and for a given task (either stated by the user or inferred from a first menu choice or other action, or from the content being created), removing or downgrading task distractions so that the user less confused, but can still access other functionality as normal if really needed.

In this case, downgrading may involve greying out elements not relevant to the current task. Hence for example if writing a letter in MS Word, whilst indicating via an accessibility profile that a low maximum score is desirable, then menu tabs relating to design, layout, references, add-ins, mailings and the like may be de-emphasised or even hidden unless the ribbon is clicked on, or until a 'Restore UI' button is clicked on (e.g. if provided when the filtering of functionality by removal or downgrade is active).

Turning now to FIG. 3, in a summary embodiment of the present description, a cognitive load assistance method comprises the following steps.

A first step s310 of providing a virtual environment (which as noted elsewhere herein may be a game environment but may alternatively be any task orientated app environment) comprising a route to complete a current task, and providing within the virtual environment one or more interactive elements (whether in-game characters, environ-mental elements, or UI elements, or the like) not essential to the current task (and hence potential distractions) that may be encountered during normal performance of the current task, as described elsewhere herein.

A second step s320 of receiving an indication (e.g. via an API, interrogation of a user assistance profile, or via an in-game or in-app assessment or UI) that cognitive load assistance is required, as described elsewhere herein.

And a third step s330 of reducing the interactivity of at least a first interactive element not essential to the current task in response to the indication, as described elsewhere herein.

It will be apparent to a person skilled in the art that variations in the above method corresponding to operation of the various embodiments of the apparatus as described and claimed herein are considered within the scope of the present invention, including but not limited to that:

the interactivity of at least the first interactive element not essential to the current task is reduced responsive to a level of assistance indicated by the received indication, as described elsewhere herein (for example in response to a value from the API, interrogation of a user assistance profile, or via an in-game or in-app assessment or UI).

the interactivity of an active interactive element, which interacts with the user without prompting by the user, is reduced to one selected from the list consisting of a passive interactive element that responds to an interaction by the user, and an element that does not respond to an interaction by the user, as described elsewhere herein. It will be appreciated that in this latter case, whilst the original interactive element is non-responsive, some alternative minimal interaction may be provided (for example after locking a door to prevent interaction with a house, the door may still prompt an interaction to say it is locked, or currently unavailable, or the like).

the interactivity of a passive interactive element that responds to an interaction by the user is reduced to an element that does not respond to an interaction by the user, as described elsewhere herein. Again some minimal alternative interaction may be provided to inform the user of the element's status.

the interactivity of an active interactive element that interacts with the user without prompting is reduced by one selected from the list consisting of removing the element from the virtual environment, and delaying the appearance of the element until the current task is complete, as described elsewhere herein. It will be appreciated that delaying the appearance of the element is effectively the same as removing it until the current task is complete.

the interactivity of a passive interactive element that responds to an interaction by the user is reduced by one selected from the list consisting of removing the element from the virtual environment and delaying the appearance of the element until the current task is complete, as described elsewhere herein. Again it will be appreciated that delaying the appearance of the element is effectively the same as removing it until the current task is complete.

a total level of non-essential interactivity over a prede-termined amount of a task (such as the whole task, a sub-task, or a unit of time or distance within a task or sub task) is evaluated based on a score for each interactive element not essential to the current task, as described elsewhere herein. As noted elsewhere, the score for an element may differ depending on whether and how it is altered, and may be based on a classification of the element or be specific to the element.

In this instance, the interactivity and associated score of one or more interactive elements not essential to the current task may be reduced until a target maximum level of non-essential interactivity over the predetermined amount of a task is met, as described elsewhere herein.

In this case, the interactivity may be reduced for a smallest number of interactive elements to meet the target, as described elsewhere herein.

Alternatively or in addition, the interactivity may be reduced whilst removing the smallest number of interactive elements, as described elsewhere herein.

Alternatively or in addition, the interactivity is reduced responsive to an order in which the interactive elements may be encountered during the task (which may be based on a known or estimated task route), as described elsewhere herein.

Alternatively or in addition, the total interactivity is reduced responsive to the remaining time available to complete the task, as described elsewhere herein.

Alternatively or in addition, the total interactivity is adjusted (potentially up or down) responsive to the level of interaction of a user with the elements not essential to the current task, as described elsewhere herein.

It will be appreciated that the above methods may be carried out on conventional hardware suitably adapted as applicable by software instruction or by the inclusion or substitution of dedicated hardware, such as the entertainment device 10.

Thus the required adaptation to existing parts of a conventional equivalent device may be implemented in the form of a computer program product comprising processor implementable instructions stored on a non-transitory machine-readable medium such as a floppy disk, optical disk, hard disk, solid state disk, PROM, RAM, flash memory or any combination of these or other storage media, or realised in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

Accordingly, and referring again to FIG. 1, in a summary embodiment of the present description a cognitive load assistance system, comprises the following.

Firstly, a virtual environment processor (for example CPU 20) adapted (for example by suitable software instruction) to provide a virtual environment (which as noted elsewhere herein may be a game environment but may alternatively be any task orientated app environment) comprising a route to complete a current task, and providing within the virtual environment one or more interactive elements (whether in-game characters, environmental elements, or UI elements, or the like) not essential to the current task that may be encountered during normal performance of the current task, as described elsewhere herein.

Secondly, an input (for example a CPU 20 in conjunction with SSD 50 and/or data port 60) adapted (for example by suitable software instruction) to receive an indication that cognitive load assistance is required (for example via an API, or a locally or remotely stored accessibility profile of the user, or via a user UI or in-app assessment), as described elsewhere herein.

And thirdly, a task interactivity processor (for example CPU 20) adapted (for example by suitable software instruction) to reduce the interactivity of at least a first interactive element not essential to the current task in response to the indication.

Instances of this summary embodiment implementing the methods and techniques described herein (for example by use of suitable software instruction) are similarly envisaged to be within the scope of the application.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method comprising:
providing a virtual environment comprising (i) a route to complete a current task, and (ii) one or more interactive elements that are not essential to completing the current task and that are encountered while completing the current task;
receiving an indication that cognitive load assistance is required; and
reducing an interactivity of one or more of the interactive elements until one or more criteria are satisfied,
wherein reducing the interactivity of one or more of the interactive elements until one or more criteria are satisfied comprises:
evaluating a total level of non-essential interactivity over a predetermined amount of a task based on a score for each interactive element that is not essential to the current task, and
wherein the interactivity and associated score of one or more interactive elements that are not essential to the current task is reduced until a target maximum level of non-essential interactivity over the predetermined amount of a task is met.

2. The method of claim 1, wherein the interactivity is reduced for a smallest number of interactive elements.

3. The method of claim 1, wherein the interactivity is reduced whilst removing the smallest number of interactive elements.

4. The method of claim 1, wherein the interactivity is reduced responsive to an order in which the interactive elements may be encountered during the task.

5. The method of claim 1, wherein the total level of non-essential interactivity is reduced responsive to the remaining time available to complete the task.

6. The method of claim 1, wherein the total level of non-essential interactivity is adjusted responsive to the level of interaction of a user with the elements that are not essential to the current task.

7. The method of claim 1, wherein reducing the interactivity of one or more of the interactive elements comprises removing an interactive element from the virtual environment.

8. The method of claim 1, wherein reducing the interactivity of one or more of the interactive elements comprises delaying an appearance of an interactive element in the virtual environment.

9. The method of claim 1, wherein reducing the interactivity of one or more of the interactive elements comprises reducing a duration of interaction for an interactive element in the virtual environment.

10. The method of claim 1, wherein reducing the interactivity of one or more of the interactive elements comprises converting an active interactive element into a passive interactive element.

11. The method of claim 10, wherein the passive interactive element responds to interactions that are initiated by a user.

12. The method of claim 1, wherein reducing the interactivity of one or more of the interactive elements comprises converting an active interactive element into a non-interactive element.

13. The method of claim 1, wherein reducing the interactivity of one or more of the interactive elements comprises converting a passive interactive element into a non-interactive element.

14. The method of claim 1, wherein the target maximum level of non-essential interactivity comprises a percentage.

15. A system comprising one or more computers and one or more storage devices on which are stored instructions that are operable, when executed by the one or more computers, to cause the one or more computers to perform operations comprising:

providing a virtual environment comprising (i) a route to complete a current task, and (ii) one or more interactive elements that are not essential to completing the current task and that are encountered while completing the current task;

receiving an indication that cognitive load assistance is required; and reducing an interactivity of one or more of the interactive elements until one or more criteria are satisfied, wherein reducing the interactivity of one or more of the interactive elements until one or more criteria are satisfied comprises:

evaluating a total level of non-essential interactivity over a predetermined amount of a task based on a score for each interactive element that is not essential to the current task, and wherein the interactivity and associated score of one or more interactive elements that are not essential to the current task is reduced until a target maximum level of non-essential interactivity over the predetermined amount of a task is met.

16. A non-transitory computer readable storage medium storing one or more computer programs configured to cause a processor-based system to execute operations comprising:

providing a virtual environment comprising (i) a route to complete a current task, and (ii) one or more interactive elements that are not essential to completing the current task and that are encountered while completing the current task;

receiving an indication that cognitive load assistance is required; and reducing an interactivity of one or more of the interactive elements until one or more criteria are satisfied, wherein reducing the interactivity of one or more of the interactive elements until one or more criteria are satisfied comprises:

evaluating a total level of non-essential interactivity over a predetermined amount of a task based on a score for each interactive element that is not essential to the current task, and wherein the interactivity and associated score of one or more interactive elements that are not essential to the current task is reduced until a target maximum level of non-essential interactivity over the predetermined amount of a task is met.

\* \* \* \* \*